US00PP10909P

United States Patent [19]

Wain

[11] Patent Number: Plant 10,909

[45] Date of Patent: May 18, 1999

[54] CHRYSANTHEMUM PLANT NAMED 'ENZO'

[75] Inventor: Peter Wain, V.R. Portsmouth, United Kingdom

[73] Assignee: Cleangro, Ltd., West Sussex, United Kingdom

[21] Appl. No.: 08/975,161

[22] Filed: Nov. 13, 1997

[51] Int. Cl.[6] ..... A01H 5/00

[52] U.S. Cl. ..... Plt./298

[58] Field of Search ..... Plt./82.5, 298

[56] References Cited

PUBLICATIONS

UPOV–ROM, Jan. 1998, Plant Variety Database, GTI Jouve Retrieval Softwear, Citation for 'Enzo'.

*Primary Examiner*—Howard J. Locker
*Attorney, Agent, or Firm*—Christie, Parker & Hale, LLP

[57] ABSTRACT

A new plant variety of Chrysanthemum producing red flowers.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'Enzo'.

The female parent of the new variety is the variety known as 'Stroika' and the male parent is a undistributed, unnamed, unpatented and undistributed seedling identified as AH9-88. The new variety has been asexually reproduced by vegetative cuttings in Ventura County, Calif. and the distinguishing characteristics are retained through successive generations of asexual reproduction.

SUMMARY OF THE INVENTION

'Enzo' is a spray type cut flower Chrysanthemum plant variety that produces red flowers and dark green foliage.

Comparison With 'Stroika'

'Enzo' differs from 'Stroika' in having a shorter response time by about 5 days, brighter red flower color and larger flower size.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of December. 'Enzo' has not been observed under all possible environmental conditions. The phenotype may vary with variations in the environment such as temperature, light intensity, day length and cultural conditions. The color description is by reference to The Royal Horticultural Society Colour Chart.

To produce a commercial product the plants may be pinched once with center bud removed. It has been observed that the shelf life of 'Enzo' is about 10 days in winter at room temperature with the response time of about 9 weeks. One treatment of growth retardant B-9 at 2000 ppm may be used. The following description is after application of growth retardant as described.

Plant

Habit: Upright.
Branching characteristics: Large number of breaks.
Number of breaks from pinch: About 3 per.
Length of lateral branches: Average — about 80 cm.
Stem color: Near 138B.

Foliage

Leaf arrangement: Alternate.
Number of leaves per lateral branch:
*Average number leaves per lateral branch.*—About 20 fully mature leaves.
(1) *Size.*—Length — Average about 11.9 cm. Width — Average about 6.7 cm.
(2) *Shape.*—Ovate.
(3) *Attachment.*—Petioled.
(4) *Apex.*—Acute.
(5) *Base.*—Tapered.

| (6) | Color: | Mature | Young |
|---|---|---|---|
| | Top: | Near 147A | Near 139A |
| | Bottom: | Near 137B | Near 137A |

Margin: Lobed/serrate.
Aspect: Very slight undulation.
Surface characteristics: Top-puberulent, bottom-puberulent.
Venation: Palmately net, main veins prominent on underside of leaf, main vein color near 143D, veinlet color near 137B.
Petiole:
(1) *Length.*—About 2.8 cm average.
(2) *Color.*—Near 138A.
Stipule: 2 per mature leaf, 2 to 3 lobed, very small and obtuse.

Flower

Inflorescence form: Cyme.
Flower form: Daisy-like.
Flower color (general): Deep red with yellow center.
Blooms: About 9 blooms average per stem.
(1) *Diameter.*—Average about 8 cm.
(2) *Depth.*—Average about 2.5 cm.
(3) *Longevity after cutting.*—About 10 days in water at room temperature.
Sepal:
(1) *Number.*—About 35.

(2) *Color.*—Near 137B.
(3) *General appearance.*—Highly membranous, short and clawed.

Peduncle:
(1) *Length.*—Average about 10 cm.
(2) *Habit.*—Straight.
(3) *Surface.*—Tomentose.
(4) *Color.*—Near 138B.
(5) *Strength.*—Medium strong.

Ray florets:
(1) *Number per flower.*—Average about 36.
(2) *Fused.*—No.
(3) *Texture.*—Smooth.
(4) *Shape.*—Elliptic.
(5) *Apex.*—3 shallow lobes.
(6) *Base.*—Tapered.
(7) *Margin.*—Entire.
(8) *Aspect.*—Very slightly reflexed back and ridged.
(9) *Length.*—Avg. About 3.6 cm.
(10) *Width.*—Avg. About 1.2 cm average.
*Color — top side.*—Immature: Near 187C. Mature: Near 46A. Fading: Near 46A — a little deeper.
*Color — under side.*—Immature: Near 178B with faint yellow streaks. Mature: Near 46A with streaks near 12A. Fading: Near 185A with yellow speckles.

Disc florets:
(1) *Number per flower.*—About 230.
(2) *Texture.*—Glossy.
(3) *Shape.*—Cylindric.
(4) *Margin.*—5-lobed with acute apex.
(5) *Length.*—About 0.7 cm.
(6) *Width.*—About 0.15 cm.
*Color.*—Immature: Near 21A. Mature: Near 16A. Fading: Near 15C.
*Fragrance.*—Fragrance of flower is stong and musky.

Reproductive Organs

Ray florets:
*Pistillate.*—(1) Pistil number: 1 per floret. (2) Ovary shape: ¾ sphere with domed and pointed top. (3) Stigma shape: Two branched. (4) Stigma color: Near 15A. (5) Style length: Average about 0.6 cm. (6) Style color: Near 1D.

Disc florets:
*Pistil.*—1 per floret. (1) Stigma shape: Forked. (2) Style length: About 0.6 cm. (3) Stigma color: Near 15A. (4) Style color: Near 154C.
*Stamens.*—(1) Stamen number: About 6. (2) Anther length: About 0.2 cm. (3) Anther shape: Linear. (4) Pollen quantity: Moderate. (5) Pollen color: Near 14A.

What is claimed is:

1. A new and distinct variety of Chrysanthemum plant substantially as herein shown and described.

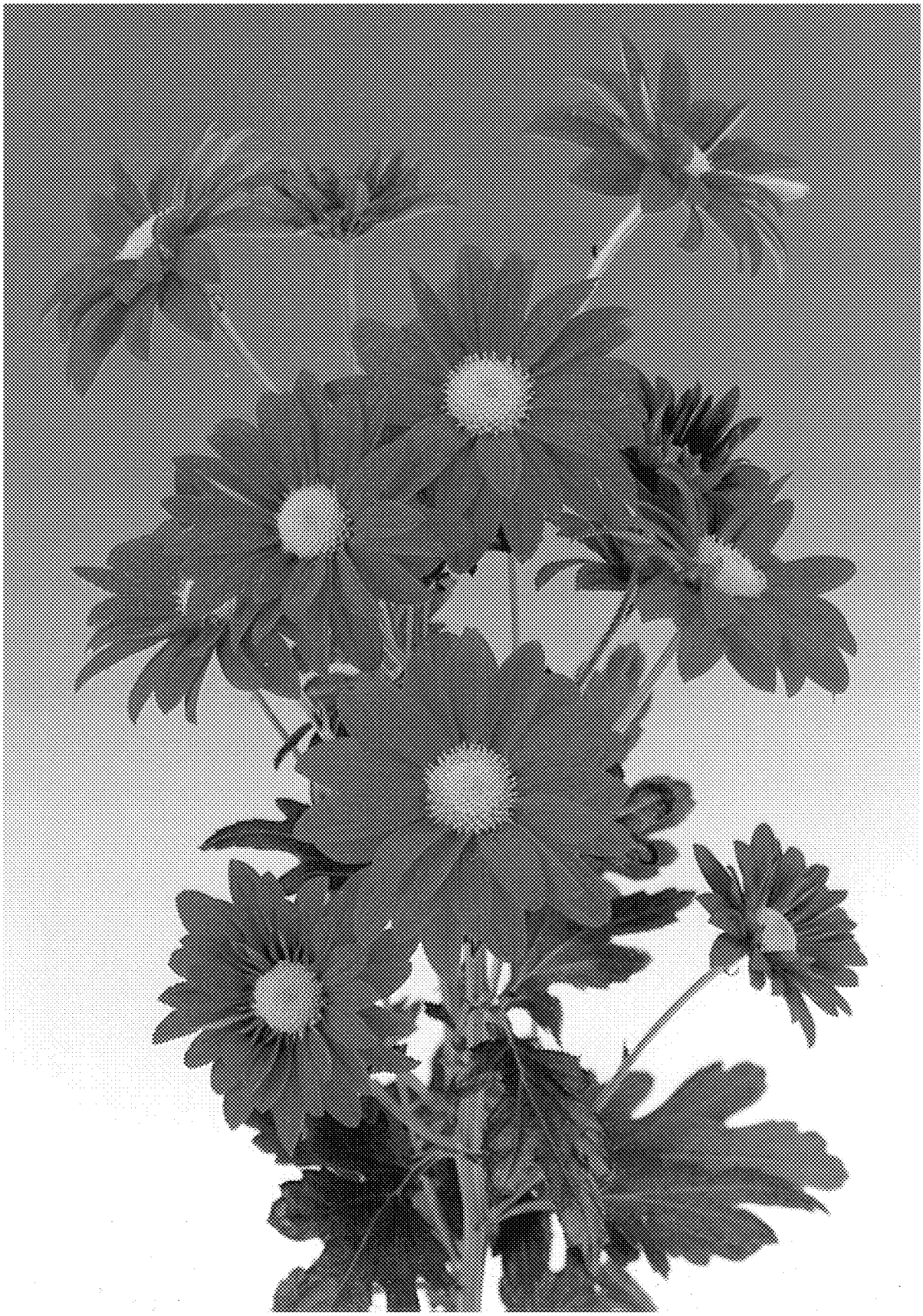

* * * * *